US00PP37054P2

(12) United States Plant Patent
van Dijk

(10) Patent No.: US PP37,054 P2
(45) Date of Patent: Oct. 21, 2025

(54) ***ANTHURIUM* PLANT NAMED 'AN2198403'**

(50) Latin Name: *Anthurium andreanum*
Varietal Denomination: AN2198403

(71) Applicant: ANTHURA B.V., Bleiswijk (NL)

(72) Inventor: Jan van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/021,869

(22) Filed: Jan. 15, 2025

(51) Int. Cl.
*A01H 5/02* (2018.01)
*A01H 6/10* (2018.01)

(52) U.S. Cl.
USPC ..... Plt./365
CPC ..... *A01H 6/10* (2018.05)

(58) Field of Classification Search
USPC ..... Plt./365
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Anthurium* plant named 'AN2198403', characterized by its upright to outwardly arching plant habit; freely clumping growth habit; bushy and dense plants; cordate dark green-colored leaves; freely flowering habit; inflorescences that are positioned within to slightly above the foliar plane on strong and mostly upright scapes; broadly cordate and glossy bright red-colored spathes; orangish yellow to yellowish white-colored spadices with tapering apices; and durable spathes that impart good inflorescence longevity.

2 Drawing Sheets

Figure 1:
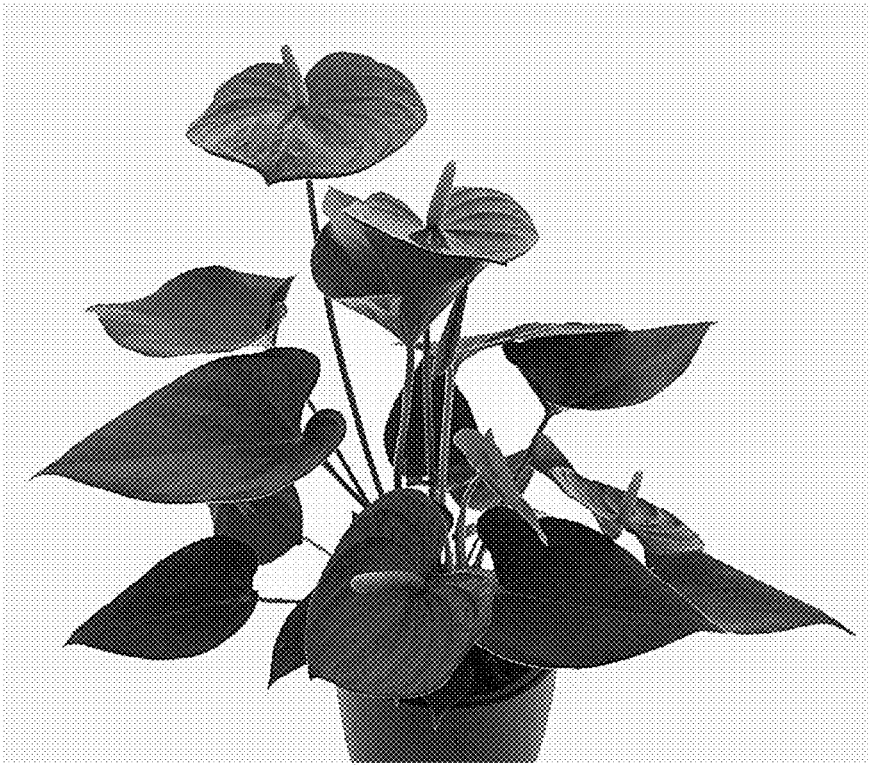

Botanical designation: *Anthurium andreanum.*
Cultivar denomination: 'AN2198403'.

CROSS-REFERENCED TO CLOSELY-RELATED APPLICATIONS

A European Community Plant Breeder's Rights application for the instant plant was filed by the Applicant/Assignee of the instant application, Anthura B.V. of Bleiswijk, The Netherlands on Nov. 20, 2024, application number 2024/2686. Foreign priority is not claimed to this application.

BACKGROUND OF THE INVENTION

The present invention relates to a new and distinct cultivar of *Anthurium* plant, botanically known as *Anthurium andreanum*, commonly referred to as Flamingo Flower and hereinafter referred to by the name 'AN2198403'.

The new *Anthurium* plant is a product of a controlled breeding program conducted by the Inventor in Bleiswijk, The Netherlands. The objective of the breeding program is to create new medium-sized and freely-clumping *Anthurium* plants with durable, glossy, and red-colored spathes.

The new *Anthurium* plant originated from a cross-pollination made by the Inventor in May 2016 in Bleiswijk, The Netherlands of *Anthurium andreanum* 'ANTHGESSIM', disclosed in U.S. Plant Pat. No. 34,251, as the female, or seed, parent with a proprietary selection of *Anthurium andreanum* identified as code number 12-028793-0002, not patented, as the male, or pollen, parent. The new *Anthurium* was discovered and selected by the Inventor as a single flowering plant within the progeny of the stated cross-pollination in a controlled greenhouse environment in Bleiswijk, The Netherlands in February 2018.

Asexual reproduction of the new *Anthurium* plant by in vitro meristem propagation in a controlled environment in Bleiswijk, The Netherlands since December 2019 has shown that the unique features of this new *Anthurium* are stable and reproduced true to type in successive generations of asexual reproduction.

SUMMARY OF THE INVENTION

Plants of the new *Anthurium* have not been observed under all possible combinations of environmental conditions and cultural practices. The phenotype may vary somewhat with variations in environment conditions such as temperature and light intensity, without, however, any variance in genotype.

The following traits have been repeatedly observed and are determined to be the unique characteristics of 'AN2198403'. These characteristics in combination distinguish 'AN2198403' as a new and distinct *Anthurium* plant:

1. Upright to outwardly arching plant habit.
2. Freely clumping growth habit; bushy and dense plants.
3. Cordate dark green-colored leaves.
4. Freely flowering habit.
5. Inflorescences that are positioned within to slightly above the foliar plane on strong and mostly upright scapes.
6. Broadly cordate and glossy bright red-colored spathes.
7. Orangish yellow to yellowish white-colored spadices with tapering apices.
8. Durable spathes that impart good inflorescence longevity.

Plants of the new *Anthurium* differ primarily from plants of the female parent, 'ANTHGESSIM', in spathe size as plants of the new *Anthurium* have broader spathes than plants of 'ANTHGESSIM'.

Plants of the new *Anthurium* differ primarily from plants of the male parent selection in spathe color as spathes of plants of the new *Anthurium* are bright red in color whereas spathes of plants of the male parent selection are pink in color. In addition, spathes of plants of the new *Anthurium* are more rugose than spathes of plants of the male parent selection.

Plants of the new *Anthurium* can also be compared to plants of *Anthurium andreanum* 'ANTHGLYNT', disclosed in U.S. Plant Pat. No. 30,967. In side-by-side comparisons, plants of the new *Anthurium* differ primarily from plants of 'ANTHGLYNT' in the following characteristics:

1. Plants of the new *Anthurium* are larger than plants of 'ANTHGLYNT'.
2. Spathes of plants of the new *Anthurium* are broader than spathes of plants of 'ANTHGLYNT'.
3. Spathes of plants of the new *Anthurium* are not as rugose as spathes of plants of 'ANTHGLYNT'.

BRIEF DESCRIPTION OF THE PHOTOGRAPHS

The accompanying photographs illustrate the overall appearance of the new *Anthurium*. The photographs show the colors as true as it is reasonably possible to obtain in colored reproductions of this type. Colors in the photographs may differ slightly from the color values cited in the detailed botanical description which accurately describe the colors of the new *Anthurium*.

The photograph on the first sheet (FIG. 1) is a side perspective view of a typical plant of 'AN2198403' grown in a container.

Figure 2:
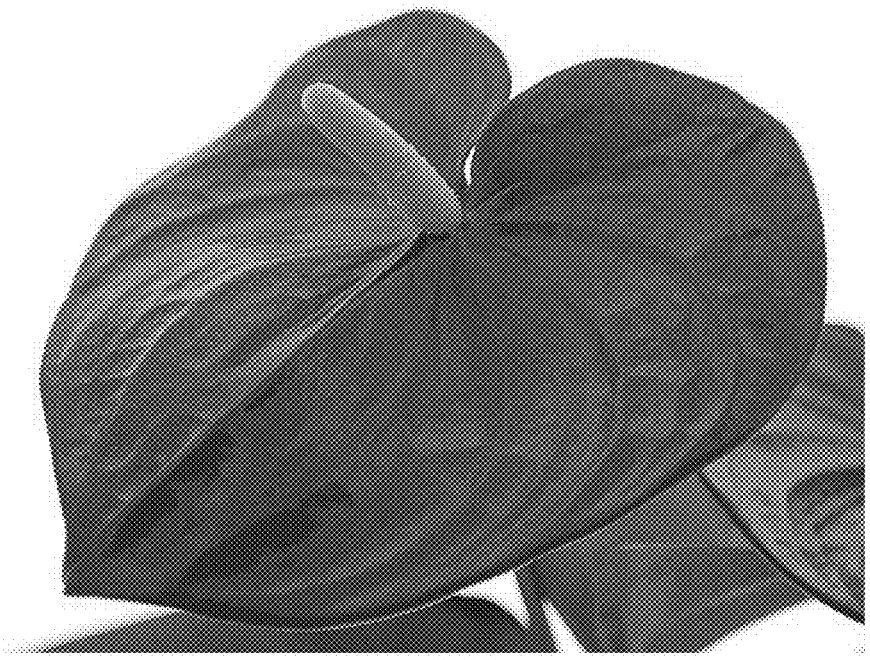

The photograph on the second sheet (FIG. 2) is a close-up view of a typical inflorescence of 'AN2198403'.

DETAILED BOTANICAL DESCRIPTION

The aforementioned photographs and following observations and measurements describe plants grown in 12-cm containers during the late autumn in a glass-covered greenhouse in Bleiswijk, The Netherlands. Plants were grown under conditions and practices which approximate those generally used in commercial *Anthurium* production. During the production of the plants, day and night temperatures ranged from about 19° C. to about 22.5° C. and light levels ranged from about 100 μmol to about 200 μmol. Plants were ten months from planting young rooted plants when the photographs and the detailed description were taken. In the following description, color references are made to The Royal Horticultural Society Colour Chart, 2015 Edition, except where general terms of ordinary dictionary significance are used.

Botanical classification: *Anthurium andreanum* 'AN2198403'.

Parentage:

*Female, or seed, parent.*—*Anthurium andreanum* 'ANTHGESSIM', disclosed in U.S. Plant Pat. No. 34,251.

*Male, or pollen, parent.*—Proprietary selection of *Anthurium andreanum* identified as code number 12-028793-0002, not patented.

Propagation:

*Type.*—By in vitro meristem propagation.

*Time to initiate roots, summer and winter.*—About two weeks at temperatures ranging from about 19° C. to about 22.5° C.

*Time to produce a rooted young plant, summer and winter.*—About six to eight weeks at temperatures ranging from about 19° C. to about 22.5° C.

*Root description.*—Medium in thickness, fibrous; typically creamy white in color slightly tinged with pink in color; actual color of the roots is dependent on substrate composition, water quality, fertilizer type and formulation, substrate temperature and physiological age of roots.

*Rooting habit.*—Freely branching, medium density.

Plant description:

*Plant shape.*—Upright to outwardly arching plant habit; overall shape, broadly ovate to broadly rhomboidal.

*Growth habit.*—Freely clumping habit imparting a bushy and dense appearance; in a single year of production, about 40 individual plants can be harvested per plant, relatively moderately vigorous to vigorous growth habit and relatively moderate growth rate.

*Plant height, from soil level to top of leaf plane.*—About 22.5 cm.

*Plant height, from soil level to top of inflorescences.*—About 40 cm.

*Plant diameter or spread.*—About 35.9 cm.

Leaf description:

*Arrangement.*—Alternate; simple; about three leaves per clump.

*Length.*—About 15.7 cm.

*Width.*—About 10.5 cm.

*Shape.*—Cordate.

*Apex.*—Acuminate with a short mucronate tip.

*Base.*—Cordate; basal lobes free and not overlapping.

*Margin.*—Entire; occasionally, slightly and coarsely undulate.

*Texture and luster, upper and lower surfaces.*—Smooth, glabrous; moderately coriaceous; glossy.

*Venation pattern.*—Pinnate.

*Color.*—Developing leaves, upper surface: Close to 146A. Developing leaves, lower surface: Close to a blend of 146A and 146B; narrow marginal edges, close to 174C. Fully expanded leaves, upper surface: Close NN137A; venation, close to 146B. Fully expanded leaves, lower surface: Close to 146B; venation, close to 144B.

*Petioles.*—Length: About 14 cm. Diameter: Distally, about 3.3 mm and proximally, about 6 mm. Strength: Strong. Texture and luster, upper and lower surfaces: Smooth, glabrous; slightly glossy. Color, upper surface: Close to a blend of 146B and 146C. Color, lower surface: Close to a blend of 144B and 146D. Geniculum length: About 2.3 cm. Geniculum diameter: About 4 mm. Geniculum texture, upper and lower surfaces: Smooth, glabrous. Geniculum color, upper surface: Close to 146A. Geniculum color, lower surface: Close to 144A. Wing length: About 1.6 cm. Wing diameter: About 4 mm. Wing color: Close to 146C; towards the apex, close to 180B.

Inflorescence Description:

*Inflorescence arrangement and flowering habit.*—Spathes with spadices; inflorescences held within and slightly above the foliar plane on strong and erect scapes; flowering structures arise from leaf axils; freely and continuous flowering year-round in controlled temperature greenhouses in The Netherlands; typically about seven developing and developed inflorescences per plant at one time; inflorescence development commences about 2.5 to 3.5 months after planting rooted young plants.

*Inflorescence longevity*.—On the plant, depending on temperature, spathes maintain good substance for about two months; inflorescences persistent.

*Fragrance*.—None detected.

*Spathes*.—Length: About 9.6 cm. Width: About 9.9 cm. Shape: Broadly cordate; slightly concave. Apex: Broadly and abruptly acute with a mucronate apex. Base: Cordate; lobes are free and not overlapping. Margin: Entire. Aspect: About 85° from the scape axis. Texture and luster, upper and lower surfaces: Smooth, glabrous; moderately coriaceous; rugose; glossy. Color: When developing, front surface: Close to 45B; mucronate apex, tinged with close to 183A. When developing, rear surface: Close to 53C; at the base, close to 48B. Fully developed, front surface: Close to 45B; mucronate apex, tinged with close to 46A; color does not change with subsequent development; venation, similar to lamina colors. Fully developed, rear surface: Close to 47D; at the base, close to 48B; color does not change with subsequent development; venation, similar to lamina colors.

*Spadices*.—Length: About 3.6 cm. Diameter: About 7.7 mm. Shape: Cylindrical, slightly tapering towards the apex; apex, obtuse; base, obtuse; in cross-section, rounded. Aspect: About 65° to 80° from the spathe axis and about 17.5° from the scape axis. Color: Immature: Close to N25D; towards the apex, close to 13B. Mature: Close to 158D; towards the base, close to 160A. Flowers: Type: Hermaphroditic. Quantity per spadix: Numerous, about 200. Height: About 0.5 mm. Diameter: About 2 mm. Shape: Roughly square. Anther color: Close to 156D. Pollen amount: Moderate. Pollen color: Close to 158D. Stigma color: Close to 164A.

*Scapes*.—Length: About 22.5 cm. Diameter: About 4 mm. Strength: Strong, sturdy. Aspect: About 20° from vertical. Color: Close to 144A tinged with close to 176D.

*Seed and fruit*.—To date, seed and fruit development has not been observed on plants of the new *Anthurium*.

Pathogen & pest resistance: To date, plants of the new *Anthurium* have not been observed to be resistant to pathogens or pests common to *Anthurium* plants.

Temperature tolerance: Plants of the new *Anthurium* have been observed to be tolerant to high temperatures of about 30° C. and to be hardy to USDA Hardiness Zone 10.

It is claimed:

1. A new and distinct *Anthurium* plant named 'AN2198403' as herein illustrated and described.

* * * * *